United States Patent [19]

Jackson

[11] Patent Number: 4,508,507
[45] Date of Patent: Apr. 2, 1985

[54] MAGNETIC DENTURE RETENTION APPARATUS

[76] Inventor: Thomas R. Jackson, 146 Renfro St., Mount Airy, N.C. 27030

[21] Appl. No.: 538,753

[22] Filed: Oct. 3, 1983

[51] Int. Cl.³ .............................................. A61C 13/22
[52] U.S. Cl. ..................................... 433/189; 433/172
[58] Field of Search ......................................... 433/189

[56] References Cited

U.S. PATENT DOCUMENTS 4,184,252  1/1980  Krol et al. ............................ 433/189
4,209,905  1/1980  Gillings ............................... 433/189

Primary Examiner—Robert Peshock
Attorney, Agent, or Firm—B. B. Olive

[57] ABSTRACT

A denture is fitted with a magnetic assembly and an operatively associated keeper. The magnetic assembly is characterized by having a magnet sandwiched between two pole elements and the pole elements and keeper are shaped with mating curved surfaces. An occlusal stop located on the keeper prevents the magnetic assembly from sliding off the keeper and prevents air gaps between the magnetic assembly and the keeper.

6 Claims, 6 Drawing Figures

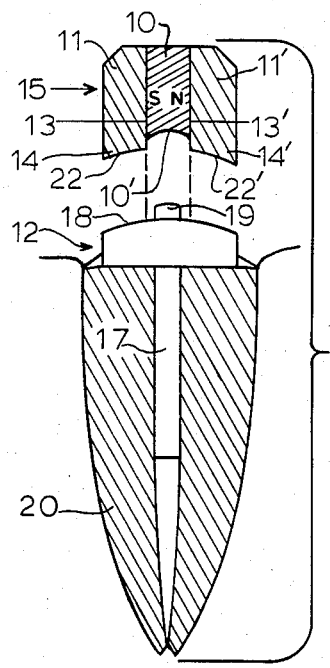
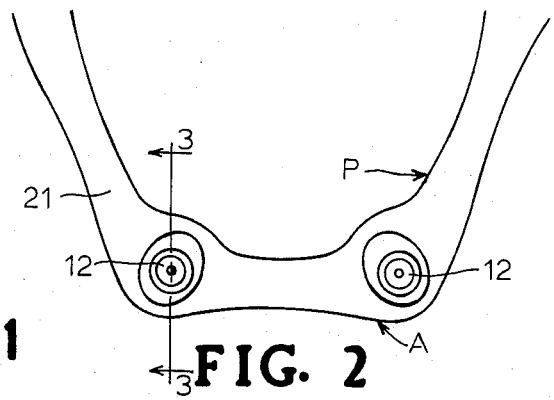
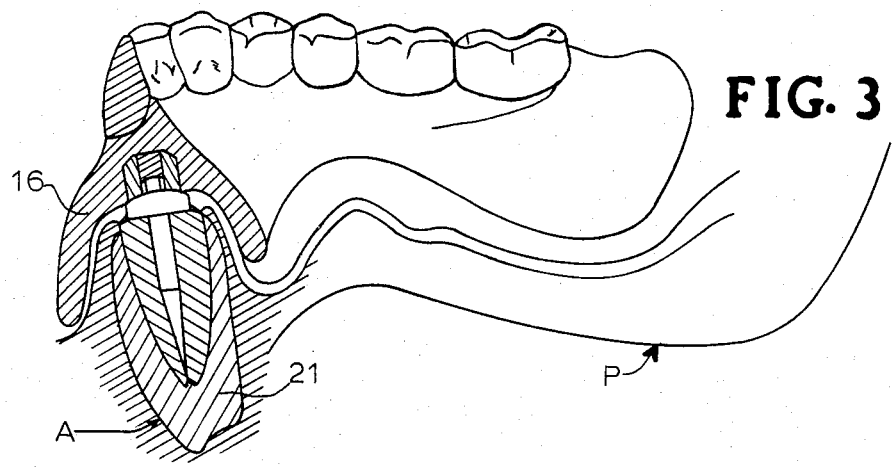
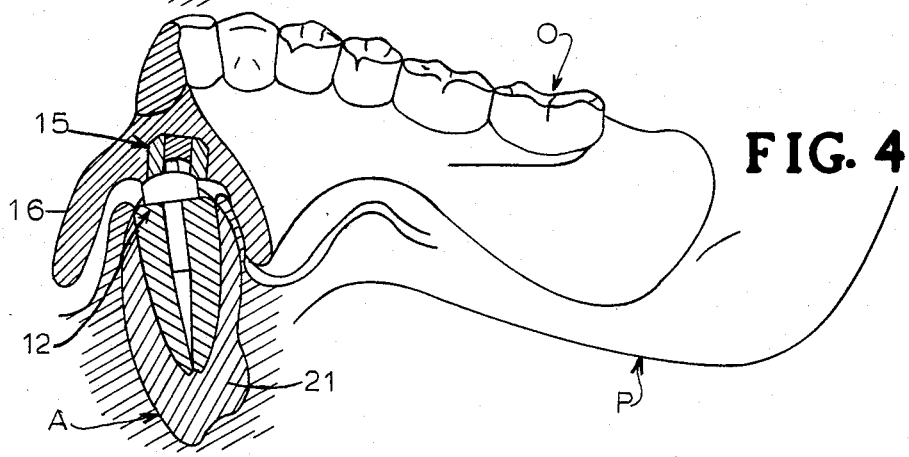
FIG. 1
FIG. 2
FIG. 3
FIG. 4

MAGNETIC DENTURE RETENTION APPARATUS

DESCRIPTION

1. Technical Field

This invention relates to denture retention generally, and in particular to an improved magnetic assembly for the retention of complete and partial dentures.

2. Background Art

U.S. Pat. Nos. 4,184,252; 4,209,905; and 4,302,189 disclose assemblies for magnetically retaining complete and partial artificial dentures in place. These references review non-magnetic means for retaining dentures, as well as earlier magnetic retention systems.

The magnetic retention system disclosed by Gillings in U.S. Pat. No. 4,209,905 comprises a first magnetic element mounted on a support associated with a person's jawbone and a second magnetic element located in the denture. When the denture is positioned in the patient's mouth, the two elements abut and retention is achieved by magnetic attraction between the elements. Gillings suggests that a U-shaped magnet be mounted in the denture and a ferromagnetic keeper element be mounted on the gum to create a closed loop magnetic flux system. A closed loop system is preferable because it avoids any possible adverse biological effects which may result from the leakage flux of an open loop system. Reference is made to Davis, A. and Rawls, W., Magnetism and Its Affect on the Living System, Exposition Press, 1980.

In the same U.S. Pat. No. 4,209,905, Gillings also illustrates the use of his system for retaining a partial denture. In this embodiment he suggests the use of locating projections to ensure the accurate reseating of the denture to the keeper. In both embodiments, however, the abutting magnet and keeper elements have flat faces.

When magnetic elements are placed in an oral cavity, it is known that the elements will corrode and wear. The second Gillings patent, U.S. Pat. No. 4,302,189, teaches the use of thin ferromagnetic pole caps to prevent magnet wear and corrosion. When pole caps are used, the magnet is completely concealed in the overdenture and is isolated from mechanical damage and chemical attack. Unfortunately, this method increases the number of parts in the magnetic element. As a result, production costs are increased and the attractive force of the completed assembly is decreased. Moreover, thin pole caps can wear through after several years of use, leaving the magnetic poles exposed.

Another disadvantage of previous magnetic retention systems is that their designs have not accounted for the consequences of occlusal loading. Occlusal loading occurs when downward pressure of the type encountered during chewing is exerted on the denture. The majority of overdentures involve the use of two mandibular cuspids. If the occlusal portion of the keeper attached to the decoronated tooth is flat, the attachment system has no play. When the posterior of the denture is loaded, an air gap develops between the magnet unit and the keeper in the anterior area of the keeper. When the occlusal loading is released, the magnet unit snaps back onto the keeper and the posterior of the denture pops up. This snapping or popping is annoying for the patient.

The Krul patent, U.S. Pat. No. 4,184,252, illustrates a magnetic retention system wherein a ferromagnetic pin having a convex surface is mounted on a decoronate natural tooth and a mating magnetic element having a concave surface is mounted in the overdenture. Such mating hemispherical surfaces, if of a larger diameter than illustrated in the Krul patent, would allow the magnet to slide laterally across the ferromagnetic pin during occlusal loading, thus preventing snap back. However, such an arrangement is not completely satisfactory, particularly when U-shaped magnets are used. Since the force required to pull a magnet off of its holding surface is substantially more than the force required to slide the magnet laterally, a magnet can easily be slid completely off its holding surface. U-shaped magnets inherently exhibit greater holding power than bar magnets when in contact with their holding surface but have less reaching power when separated from their holding surface. Reference is made to Moskowitz, L. R., Permanent Magnet Design and Application Handbook, Cahners Books International, Inc., 1976. Moreover, U-shaped magnets have a reduced holding surface area because of the gap between the two pole end faces. Therefore, a U-shaped magnet unit would only have to be slid a short distance across its keeper surface before one pole face would break contact with the keeper surface, thus creating an undesirable open flux circuit and once contact between the magnet unit and keeper surface was broken, the magnet would be less likely to have what is referred to as reaching power and which is necessary to restore contact.

It would therefore be desirable to have a closed flux loop magnetic retention system with few parts, with greater attractive force, and which protects the magnet itself from chemical and physical damage. It would further be desirable to have such a system with enough play in it to prevent annoying snap back, but which will not allow the magnet unit to slide laterally completely off of the keeper surface. The achieving of such an improved system is thus an object of this invention.

DISCLOSURE OF INVENTION

In accordance with the present invention, applicant provides a magnet unit and keeper assembly having mating surfaces of selected concave or convex curvature. The magnet unit is comprised of a magnet and two pole structures assembled in a sandwich arrangement. When the magnet structure is cemented into an overdenture and the site filled with acrylic, only the two hemispherically-shaped pole ends of the pole structure are exposed. Thus, the magnet is completely concealed, and only three parts are used in the construction of the magnet unit. The attractive force of the assembly is substantially enhanced.

The keeper is cemented into a decoronate natural tooth, cast into a coping or, for a partial denture, incorporated into the cast abutment crown. The surfaces of the keeper mate the surfaces of the pole ends of the magnet unit. When occlusal loading occurs, the mated curved surfaces allow the magnet unit to slide across the face of the keeper without creating an air gap. An occlusal stop is provided to prevent the magnet unit from sliding completely off of the keeper.

DESCRIPTION OF THE DRAWINGS

FIG. 1 is a side elevation section view of the magnetic retention assembly with the keeper mounted in a decoronated tooth.

FIG. 2 is a top plan view representing a portion of a patient's lower jaw and illustrating a typical keeper arrangement.

FIG. 3 is a fragmentary section view of the retention system with the denture in place in the patient's jaw and taken in a direction generally corresponding to line 3—3 of FIG. 2.

FIG. 4 repeats the view shown in FIG. 3 but illustrating the effect on the invention magnetic retention system of occlusal loading in the posterior of the overdenture.

BEST MODE FOR CARRYING OUT THE INVENTION

Figure 5:
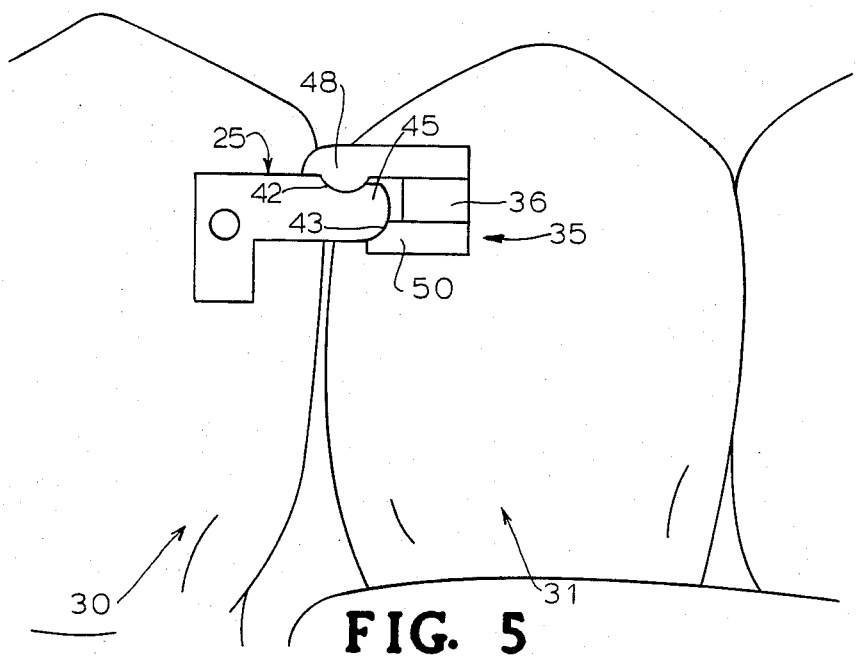
FIG. 5 is a schematic side view of the invention magnetic retention system for partial dentures.

A magnetic dental retention assembly as shown in FIGS. 1-4 consists of a magnet unit 15 and a keeper 12. The magnet unit is comprised of a magnet 10 and two end pole elements 11, 11'. In the preferred embodiment, the magnet 10 is a rare earth magnet of the cobalt-samarium type. The pole elements 11, 11' are preferably constructed of type 444 9/2 ferritic stainless steel, a castable magnetizable alloy. The keeper 12 is preferably constructed of type 400 stainless steel. Nevertheless, any materials having the appropriate magnetic, ferromagnetic, and corrosive resistant properties may be used.

The respective spaced poles 13, 13' of the magnet 10 are positioned horizontally to abut the pole elements 11, 11'. The pole elements 11, 11' are rigidly sandwiched to the magnet 10. By locating the pole elements vertically as in FIGS. 1-4 instead of horizontally, the possibility of magnetic flux leakage axially to the gingival tissues is minimized. Moreover, this design produces a magnet unit with inherently greater holding power.

The pole elements 11, 11' have pole ends 14, 14' which extend outward from the magnet 10 and terminate with concave faces 22, 22'. When the magnet unit 15 is mounted in a completed denture 16, as illustrated in FIG. 3, only the pole ends will protrude through the denture base. Concave bottom face 10' of the magnet 10 can be covered by partially filling the gap between the pole ends 14, 14' with acrylic or other suitable material while leaving room for entry of occlusal stop 19.

The keeper 12 consists of an endodontic post 17, a hemispherical surface 18 and a centrally located protruding occlusal stop 19. In the illustrated form of FIG. 1, the keeper 12 is fastened into a decoronated and root canal filled tooth 20. The keeper 12 can be cemented into the tooth 20 by preparing a hole with a black "Whaledent" type para-post drill and using glass ionomer cement and with appropriate treatment of the exposed dentin.

FIG. 2 illustrates a typical keeper arrangement in a patient's lower jaw 21. The anterior of the jaw is indicated by letter A and the posterior of the jaw is indicated by letter P. The keepers 12 are located in the anterior of the jaw, usually over the canine teeth.

Functioning of the convex hemispherical keeper face 18, the concave hemispherical pole end faces 22, 22' and the convex faced occlusal stop 19, is best illustrated by FIGS. 3 and 4.

FIGS. 3 and 4 illustrate the magnet unit 15 incorporated into a complete overdenture 16, with the overdenture 16 resting on a patient's lower jaw 21. When the overdenture 16 is so installed, the magnet unit 15 abuts the keeper 12 and stop 19 is positioned between the pole ends 14, 14'. Actual contact between the keeper face 18 and the pole end faces 22 is made, and the assembly is thus held together magnetically.

In FIG. 3 there is no occlusal loading in the posterior of the overdenture. In FIG. 4, occlusal loading has occurred because of downward pressure exerted at the point designated by letter O, thus causing the magnet unit 15 to slide laterally across the hemispherical keeper face. Further lateral movement is precluded, however, when the occlusal stop 19 is brought in contact with the pole end 14. Since the magnet unit was able to slide laterally, no air gap formed between the pole faces 22, 22' and the hemispherical keeper surface 18. Thus, when the occlusal pressure O is released, the magnet unit 15 will merely slide back to the position indicated in FIG. 3, and there will be no annoying popping or snap back.

Figure 6:
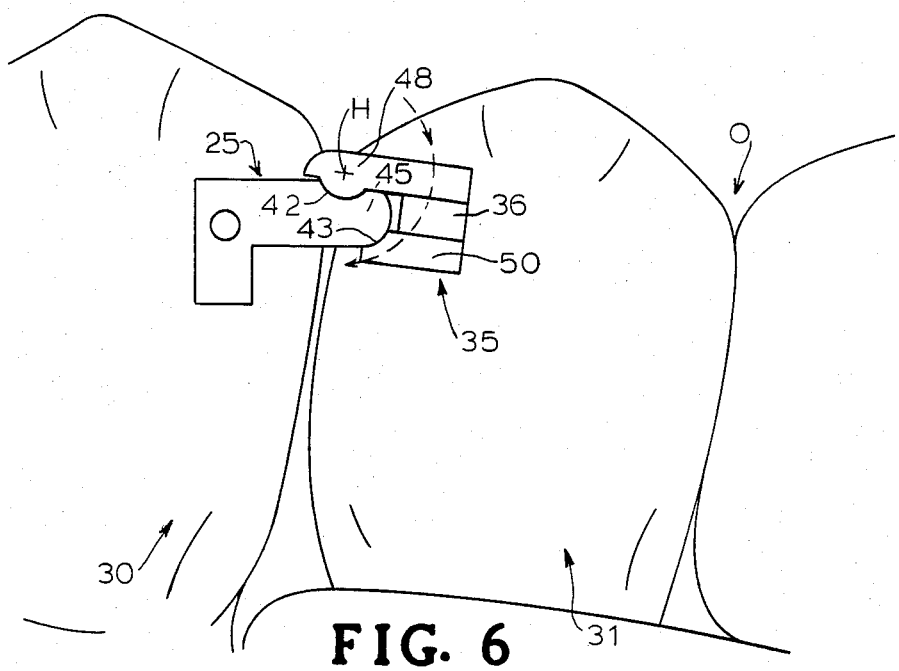
FIG. 6 repeats the view shown in FIG. 5 but illustrating the effect of occlusal loading.

An alternate embodiment of the invention for partial dentures is illustrated in FIG. 5. In FIG. 5, the L-shaped keeper 25 is incorporated into the distal surface of the casted abutment crown 30, and the magnet unit 35 is cured into the removable prosthesis 31. The keeper 25 has a concave hemispherical keeper surface 42, a convex hemispherical keeper surface 43, and an occlusal stop 45. The magnet unit 35 has a magnet 36, an upper convex faced hemispherical pole end 48, and a lower concave faced hemispherical pole member 50. Both embodiments of the invention are formed of similar materials. When the magnet assembly of the alternate embodiment is in place as seen in FIG. 5 and the corresponding hemispherical surfaces are mated as seen in FIG. 5, occlusal loading O as seen in FIG. 6 will cause the magnet unit to rotate a few degrees on hinge axis H before the occlusal stop 45 is brought into contact with the upper pole end 48 and precludes further movement. This arrangement again prevents annoying snap-back or popping during occlusal loading. Removal of loading O restores the assembly to the position of FIG. 5.

What is claimed is:

1. A denture comprising:
   (a) a base member having at least one artificial tooth mounted therein;
   (b) a magnetic assembly embedded in said base member and comprising:
      (i) a singular bar magnet having opposed, laterally spaced apart, side pole faces and opposed end surfaces; and
      (ii) a pair of magnetic flux transmitting pole members rigidly secured to said magnet on opposite sides thereof and sandwiching said magnet therebetween with said magnet side pole faces in abutting relation to respective conforming surfaces of said pole members so as not to define any space therebetween, said pole members each having end portions extending outwardly from one end surface of said magnet in a form enabling said magnet to be completely embedded in said base member with said pole member end portions protruding therefrom, said pole member end portions terminating with at least portions thereof formed with surfaces of selected curvature; and
   (c) a magnetic flux transmitting keeper element formed in a manner enabling said keeper element to be secured to mouth structure mating said base member when said denture is in place, said keeper element being formed with a selected number of curved surfaces mating said pole member surfaces in a slidable relation and being shaped for operative relation with said pole members such that during occlusion loading of said base member said assembly may rotate at least slightly with respect to said keeper without creating an air gap between the engaging mated curved surfaces of said keeper and pole members.

2. A denture as claimed in claim 1 wherein said pole member surfaces are concave and in a common plane and said selected number of keeper surfaces comprise a single convex surface.

3. A denture as claimed in claim 1 wherein one said pole member end portion is formed with a concave surface, another said pole member end portion is formed with a convex surface and said keeper element is formed with mating convex and concave surfaces.

4. A denture comprising:
(a) a base member having at least one artificial tooth mounted therein;
(b) a magnetic assembly embedded in said base member and comprising:
  (i) a bar magnet having opposed, spaced apart, side pole faces and opposed end surfaces; and
  (ii) a pair of magnet flux transmitting pole members rigidly secured to said magnet on opposite sides thereof in sandwich relation with said magnet pole faces in abutting relation to respective conforming surfaces of said pole members, said pole members each having end portions extending outwardly from one end surface of said magnet in a form enabling said magnet to be completely embedded in said base member with said pole member end portions protruding therefrom; said pole member end portions terminating with at least portions thereof formed with surfaces of selected curvature; and
(c) a magnetic flux transmitting keeper element formed in a manner enabling said keeper element to be secured to mouth structure mating said base member when said denture is in place, said keeper element being formed with a selected number of curved surfaces mating said pole member surfaces in a slidable relation and being shaped for operative relation with said pole members such that during occlusion loading of said base member said assembly may rotate at least slightly with respect to said keeper without creating an air gap between the engaging mated curved surfaces of said keeper and pole members and said keeper element further being formed with stop means to limit said rotation.

5. A denture comprising:
(a) a base member having at least one artificial tooth mounted therein;
(b) a magnetic assembly embedded in said base member and comprising:
  (i) a bar magnet having opposed, spaced apart, side pole faces and opposed end surfaces; and
  (ii) a pair of magnetic flux transmitting pole members rigidly secured to said magnet on opposite sides thereof in sandwich relation with said magnet pole faces in abutting relation to respective conforming surfaces of said pole members, said pole members each having end portions extending outwardly from one end surface of said magnet in a form enabling said magnet to be completely embedded in said base member with said pole member end portions protruding therefrom, said pole member end portions terminating with at least portions thereof formed with surfaces of selected curvature; and
(c) a magnetic flux transmitting keeper element formed in a manner enabling said keeper element to be secured to mouth structure mating said base member when said denture is in place, said keeper element being formed with a selected number of curved surfaces mating said pole member surfaces in a slidable relation and being shaped for operative relation with said pole members such that during occlusion loading of said base member said assembly may rotate at least slightly with respect to said keeper without creating an air gap between the engaging mated curved surfaces of said keeper and pole members and wherein said keeper element is formed with an occlusal stop shaped so that movement of said assembly in relation to said keeper element is precluded when either said pole member end portion contacts said stop.

6. A denture comprising:
(a) a base member having at least one artificial tooth mounted therein;
(b) a magnetic assembly embedded in said base member and comprising:
  (i) a bar magnet having opposed, spaced apart, side pole faces and opposed end surfaces; and
  (ii) a pair of magnetic flux transmitting pole members rigidly secured to said magnet on opposite sides thereof in sandwich relation with said magnet pole faces in abutting relation to respective conforming surfaces of said pole members, said pole members each having end portions extending outwardly from one end surface of said magnet in a form enabling said magnet to be completely embedded in said base member with said pole member end portions protruding therefrom, said pole member end portions terminating with at least portions thereof formed with concave surfaces of selected curvature in a common plane; and
(c) a magnetic flux transmitting keeper element formed in a manner enabling said keeper element to be secured to mouth structure mating said base member when said denture is in place, said keeper element being formed with a single convex surface and having an occlusal stop comprising a centrally located, outwardly extending protrusion from said convex surface, said single convex surface mating said pole member surfaces in a slidable relation and being shaped for operative relation with said pole members such that during occlusion loading of said base member said assembly may rotate at least slightly with respect to said keeper without creating an air gap between the engaging mated curved surfaces of said keeper and pole members.

* * * * *